US012672811B2

(12) United States Patent
Jeong

(10) Patent No.: US 12,672,811 B2
(45) Date of Patent: Jul. 7, 2026

(54) BIO-SIGNAL MEASUREMENT PATCH DEVICE AND METHOD OF USING THE SAME

(71) Applicant: ATSENS CO., LTD., Gyeonggi-do (KR)

(72) Inventor: Jong Ook Jeong, Gyeonggi-do (KR)

(73) Assignee: ATSENS CO., LTD., Gyeonggi-Do (KR)

( * ) Notice: Subject to any disclaimer, the term of this patent is extended or adjusted under 35 U.S.C. 154(b) by 256 days.

(21) Appl. No.: 18/347,760

(22) Filed: Jul. 6, 2023

(65) Prior Publication Data

US 2024/0041374 A1      Feb. 8, 2024

(30) Foreign Application Priority Data

Aug. 2, 2022      (KR) ........................ 10-2022-0096107

(51) Int. Cl.
*A61B 5/257* (2021.01)
*A61B 5/00* (2006.01)
*A61B 5/0205* (2006.01)

(52) U.S. Cl.
CPC ............ *A61B 5/257* (2021.01); *A61B 5/0205* (2013.01); *A61B 5/6833* (2013.01)

(58) Field of Classification Search
CPC ....... A61B 5/257; A61B 5/6833; A61B 5/256; A61B 5/282; A61B 5/251; A61B 5/6843; A61B 2562/14; A61B 2562/164
See application file for complete search history.

(56) References Cited

U.S. PATENT DOCUMENTS

| | | | |
|---|---|---|---|
| 8,849,369 B2 * | 9/2014 | Cogan | A61N 1/36082 |
| | | | 607/116 |
| 11,253,203 B2 | 2/2022 | Yang | |
| 2007/0038257 A1 * | 2/2007 | Gray | A61B 5/6843 |
| | | | 607/8 |
| 2012/0245436 A1 * | 9/2012 | Rutkove | A61B 5/053 |
| | | | 600/301 |
| 2014/0148678 A1 * | 5/2014 | Drori | A61B 5/282 |
| | | | 600/389 |
| 2016/0095527 A1 * | 4/2016 | Thng | A61B 5/339 |
| | | | 600/382 |
| 2016/0113535 A1 * | 4/2016 | Marek | A61B 5/25 |
| | | | 600/523 |
| 2019/0239769 A1 * | 8/2019 | Lee | A61B 5/0006 |

(Continued)

FOREIGN PATENT DOCUMENTS

| | | |
|---|---|---|
| JP | 2017213391 A | 12/2017 |
| KR | 20120084950 A | 7/2012 |

(Continued)

OTHER PUBLICATIONS

Notice of Reasons for Refusal for Corresponding Japanese Patent Application No. 2023-120005, mailed Jul. 2, 2024, 5 pages.

*Primary Examiner* — Nathan J Jenness
(74) *Attorney, Agent, or Firm* — Bridgeway IP Law Group, PLLC; Sang Ho Lee; Hyun Woo Shin

(57)      ABSTRACT

A bio-signal measurement patch device includes a substrate formed of a flexible material, a housing arranged in a first region of the substrate, a bio-signal measurement sensing electrode arranged in a second region of the substrate, and a slit formed in the substrate to divide the first region and the second region.

13 Claims, 8 Drawing Sheets

(56)        References Cited

U.S. PATENT DOCUMENTS

2021/0169390 A1     6/2021  Kim et al.
2023/0000436 A1*    1/2023  Chae ...................... A61B 5/282

FOREIGN PATENT DOCUMENTS

KR      20140050374  A     4/2014
KR      20200033417  A     3/2020
KR      20210071607  A     6/2021
KR      20220048625  A     4/2022

* cited by examiner

BIO-SIGNAL MEASUREMENT PATCH DEVICE AND METHOD OF USING THE SAME

This application is based on and claims priority under 35 U.S.C. § 119 to Korean Patent Application No. 10-2022-0096107, filed on Aug. 2, 2022, in the Korean Intellectual Property Office, the disclosure of which is incorporated by reference herein in its entirety.

BACKGROUND

1. Field

The disclosure relates to a bio-signal measurement patch device configured to measure bio-signals such as an electrocardiogram signal and use the bio-signals for healthcare management, and a method of using the bio-signal measurement patch device.

2. Description of the Related Art

As an economic level and aging population increase, there has been an increased public interest in a healthcare management by physical activities and regular sport activities. For the healthcare management, it is required to develop a bio-signal measurement apparatus including a sensor configured to constantly measure bio-signals such as electrocardiogram (ECG) signals, respiration signals, a heart pulse wave, and electromyogram signals related to the movements of body muscles.

For example, an electrocardiogram (ECG), which is one of well-known biometric data, is a record of an action voltage generated according to a contraction and an expansion of a heart muscle according to a heartbeat. The ECG is acquired by using a method of measuring an action voltage according to the contraction of the heart muscle by attaching an electrode to body skin and depicting measured data as a graph.

The ECG is used to detect a heart condition and also used as a basic measurement method for diagnosis of heart diseases such as angina, cardiac infarction, and arrhythmia.

To measure the ECG as described above, an ECG sensor electrode maintains a close contact with a skin of a patient, which is the same with or similar to use of an electromyography (EMG) sensor electrode configured to measure an electromyogram and a sensor configured to measure a respiration signal. However, due to a decrease in adhesion over time, a curved shape of a human body, and limitation in adhesives applicable to the human body, a quality of measured signals becomes poor. Therefore, sufficient adhesion may be needed to maintain attachment of the sensors to the skin.

A bio-signal measurement apparatus described in U.S. Pat. No. 11,337,632 is shown in FIG. 1. Referring to FIG. 1, a housing 20, including a battery and measuring electronics, and an electrode 30 are fixed on a substrate 10, and are connected to each other through a wire. In this case, the substrate 10 is flexible. However, the housing 20 is not easily attached to a human body due to its rigidity. Furthermore, the housing 20 is pushed in the direction of gravity by the weight of the housing injection molding and the battery. As a result, the adhesion strength of other portions of the substrate 10 to the skin may decrease.

To solve the aforementioned problem, the patent document 1 discloses a structure in which an attachment portion 12 is formed only in a portion of the substrate 10 in which the electrode 30 is formed, and not in the housing 20 and a portion 11 between the housing 20 and the electrode 30, in order to separate an attachment area. However, in this case, the substrate 10 may be attached to the body of the user in a state where the housing 20 wavers, and due to a weight of the housing. There is a limitation in preventing the substrate 10 from being separated from the body.

The background art described above may include technical information held by the inventors for derivation of the disclosure or obtained in a derivation process of the disclosure, and is not necessarily a well-known technology disclosed to public before application of the disclosure.

SUMMARY

The disclosure provides a bio-signal measurement patch device and a method of using the same, whereby an attachment quality improvement tool may maintain an attachments state of sensors to skin for measuring bio-signals. However, this is only an example, and technical goals of the disclosure are not limited thereto.

Additional aspects will be set forth in part in the description which follows and, in part, will be apparent from the description, or may be learned by practice of the presented embodiments of the disclosure.

Various embodiments of the present disclosure provides a bio-signal measurement patch device as follows.

In various embodiments, a bio-signal measurement patch device includes a substrate including a flexible material, a housing arranged in a first region of the substrate, and a bio-signal measurement sensing electrode arranged in a second region of the substrate. One or more slits are formed in a penetrating manner, on the substrate, in a direction dividing the first region and the second region.

In at least one variant, a plurality of slits may be serially formed and a bridge connecting the first region to the second region may be formed among the plurality of slits.

In another variant, the bio-signal measurement patch device may further include a reference electrode disposed on the substrate or in the housing, and a skin attachment sensing electrode being arranged on the substrate and configured to measure attachment quality of the bio-signal measurement sensing electrode according to a change in a capacitance of the skin attachment sensing electrode and the reference electrode.

In another variant, the reference electrode may be arranged in the first region or may be embedded in the housing, and the skin attachment sensing electrode may be arranged in the second region.

In another variant, a plurality of skin attachment sensing electrodes may be arranged at a position surrounding the bio-signal measurement sensing electrode.

In another variant, a plurality of the bio-signal measurement sensing electrodes may be arranged in the second region of the substrate, and a plurality of skin attachment sensing electrodes may be alternately arranged among the plurality of bio-signal measurement sensing electrodes.

In another variant, the skin attachment sensing electrode may be additionally arranged in the first region, and a distance between the skin attachment sensing electrode arranged in the first region and the one or more slits may be less than a distance between the one or more slits and a center of the housing.

Furthermore, the bio-signal measurement sensing electrode may further include at least one of a respiratory sensor, an electrocardiogram sensor, a snore sensor, a tossing-and-turning sensor, an electromyogram sensor, a temperature sensor, and an impedance sensor.

In another variant, the first region may be arranged in a lower region of the substrate, and the second region may be arranged in an upper region of the substrate.

In various embodiments, a method of using a bio-signal measurement patch device, in which the bio-signal measurement patch device described above is used. The method includes a substrate arrangement operation to arrange a surface of a substrate on which the housing and a bio-signal measurement electrode are arranged at a portion of a heart of a user, and an attachment operation of attaching the substrate onto the skin of user by using an attachment patch attached on another surface of the substrate. In the substrate arrangement operation, the substrate may be arranged such that the first region is lower than the second region.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
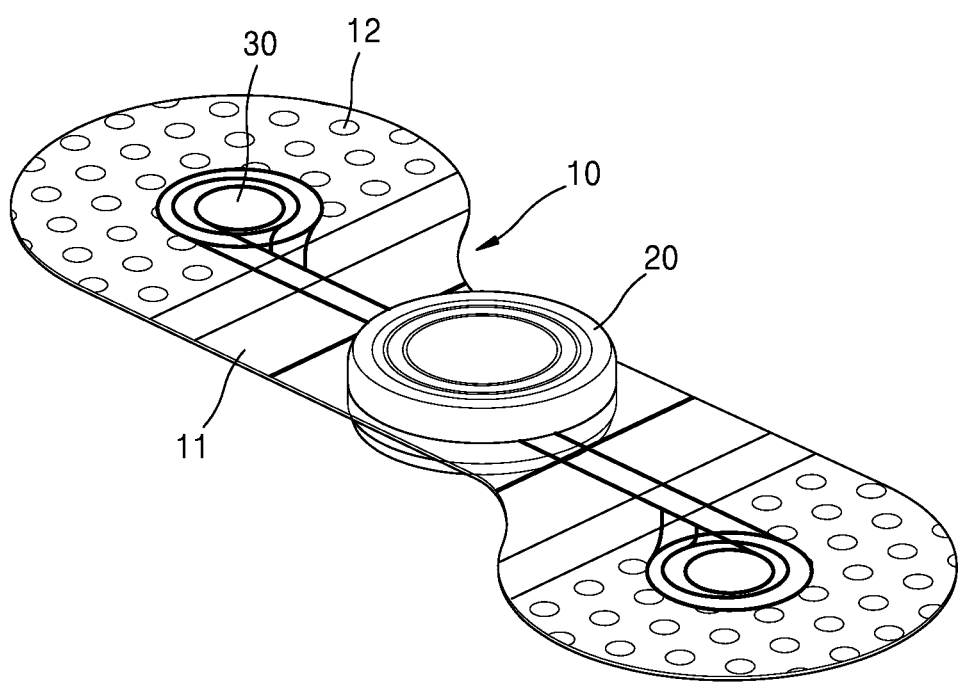
FIG. 1 is a perspective view of a conventional ECG electrode patch device.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

In following embodiments, terms such as "first," "second" are not used in a limited sense, but are used distinguish one component from another component.

In following embodiment, unless the context clearly indicate otherwise, singular forms are intended to plural forms as well.

In addition, terms such as "include," "comprise," and "have" indicate existence of features or components described in the specification, and are not to preclude addition of one or more other features or components.

In the drawings, for convenience of explanation, sizes of components may be exaggerated or reduced. For example, sizes and thickness of the components in the drawings are arbitrarily illustrated for convenience of explanation, and therefore, the disclosure is not limited to the illustration.

In the following embodiments, the x axis, the y axis, and the z axis are not limited to three axes on an orthogonal coordinate system and may be interpreted as a broader sense. For example, the x axis, the y axis, and the z axis may be orthogonal to one another, but may also refer to different directions not orthogonal to one another.

When a certain embodiment may be implemented differently, a specific process order may be performed differently from the described order. For example, two consecutively described processes may be performed substantially at the same time or performed in an order opposite to the described order.

Terms used in the present application is only used to describe specific embodiments and are not to limit the disclosure. In the present application, it will be understood that terms such as "comprise," "include," or "have" indicates presence of features, numbers, steps, operations, components, elements, or combinations thereof and are not to preclude existence or addition of one or more other features, numbers, steps, operations, members, components, or combinations thereof.

In the present disclosure, the monitoring device is an electronic device including a processor, memory, and communication module, and may include devices such as a desktop, a smart phone, a mobile phone, a laptop, and a tab. The monitoring device may communicate with the bio-signal measurement patch device and receive data on the bio-signal measured by the bio-signal measurement patch device.

Hereinafter, detailed embodiments will be described in detail with reference to the accompanying drawings.

Figure 2:
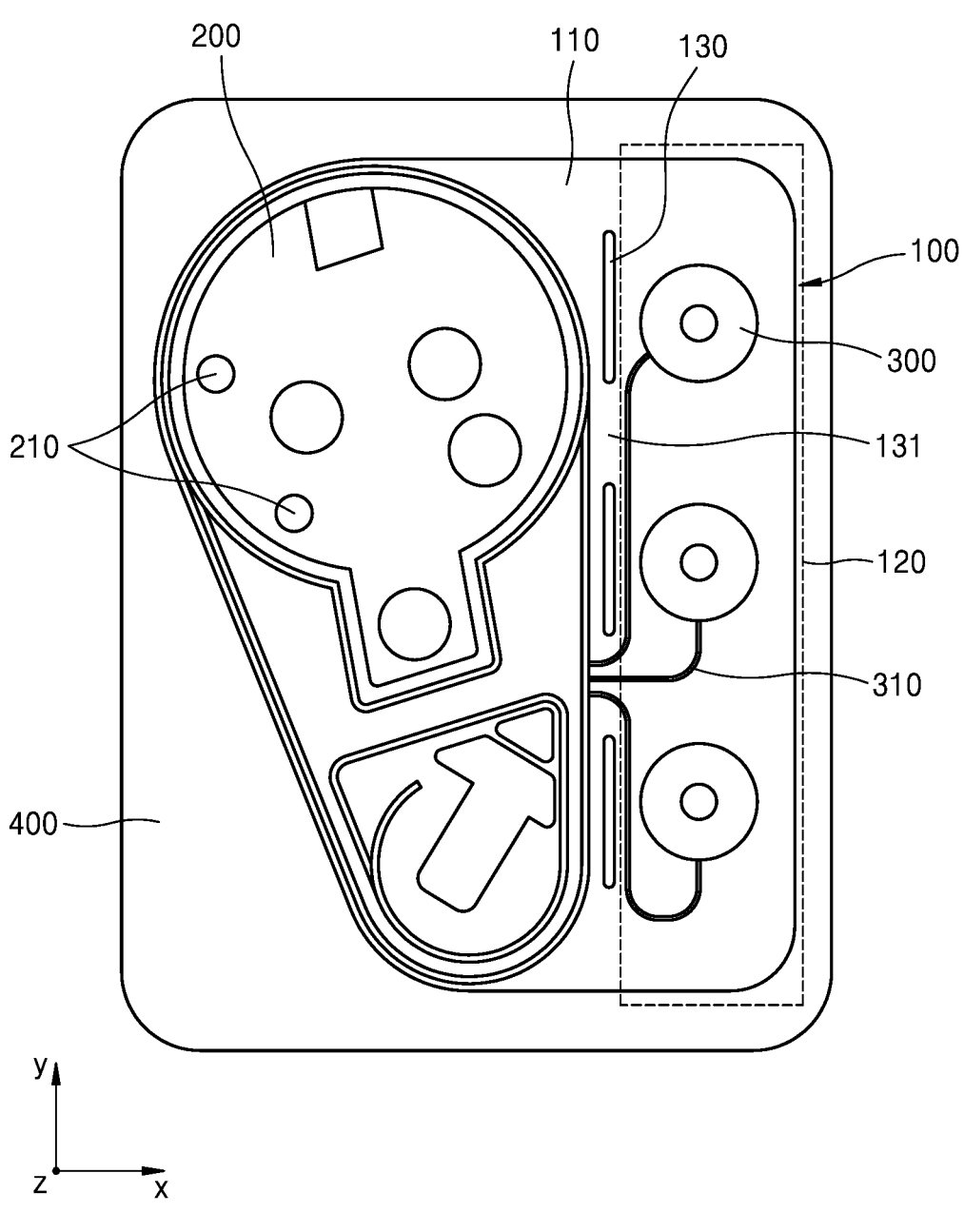
FIG. 2 is a top-plan view of a bio-signal measurement patch device according to one or more embodiments of the present disclosure.
Figure 3A:
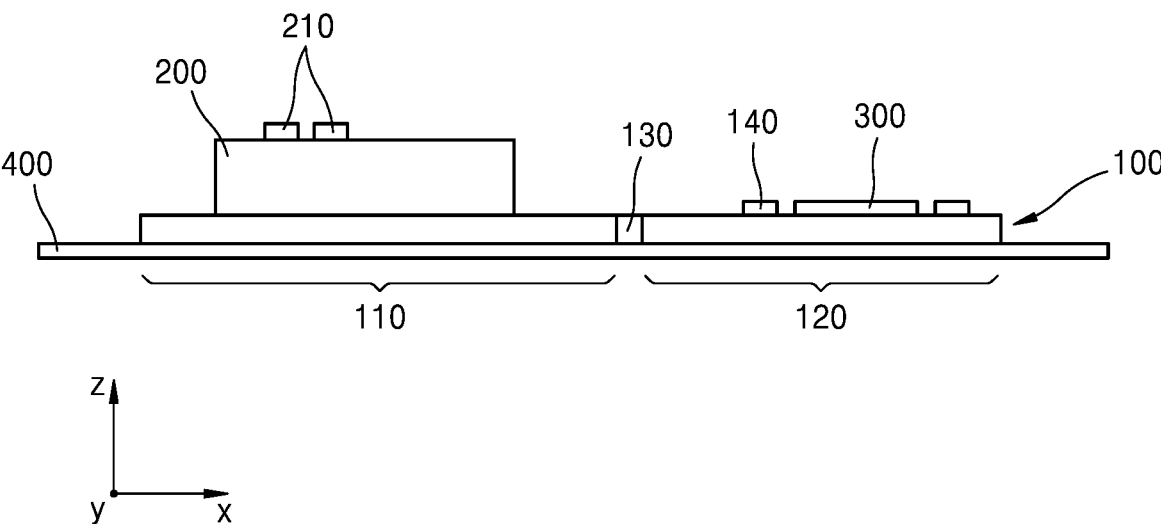
FIG. 3A is a right-side view of the bio-signal measurement patch device according to one or more embodiment of the present disclosure.
Figure 3B:
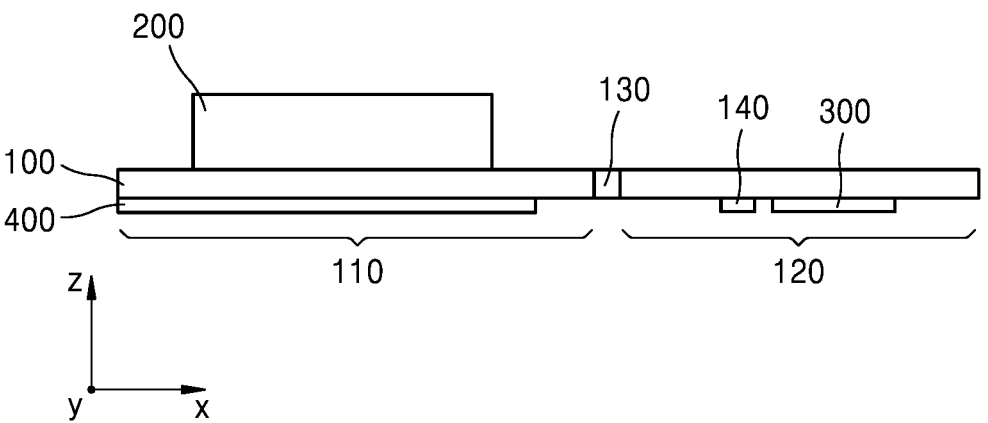
FIG. 3B is a right-side view of the bio-signal measurement patch device according to another embodiment of the present disclosure.
Figure 4:
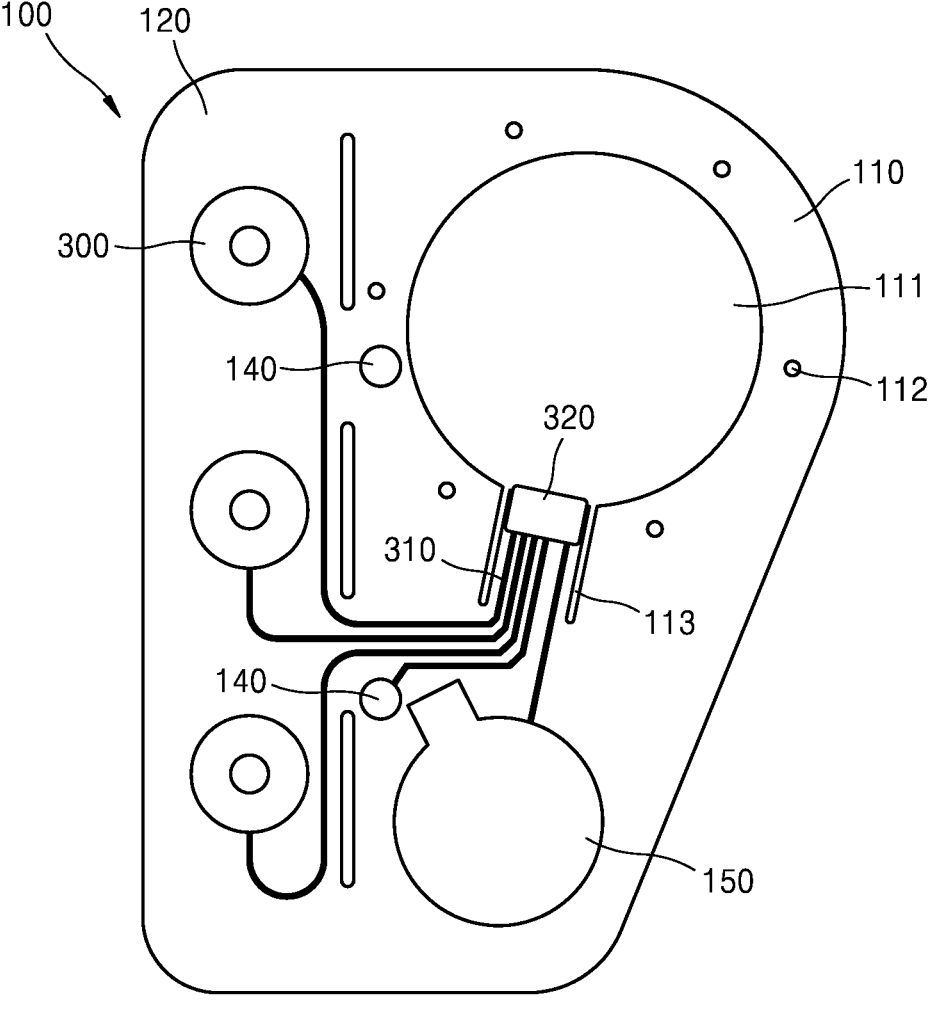
FIG. 4 is a bottom view of a skin attachment sensing electrode arranged in a first region shown in FIG. 2.
Figure 5:
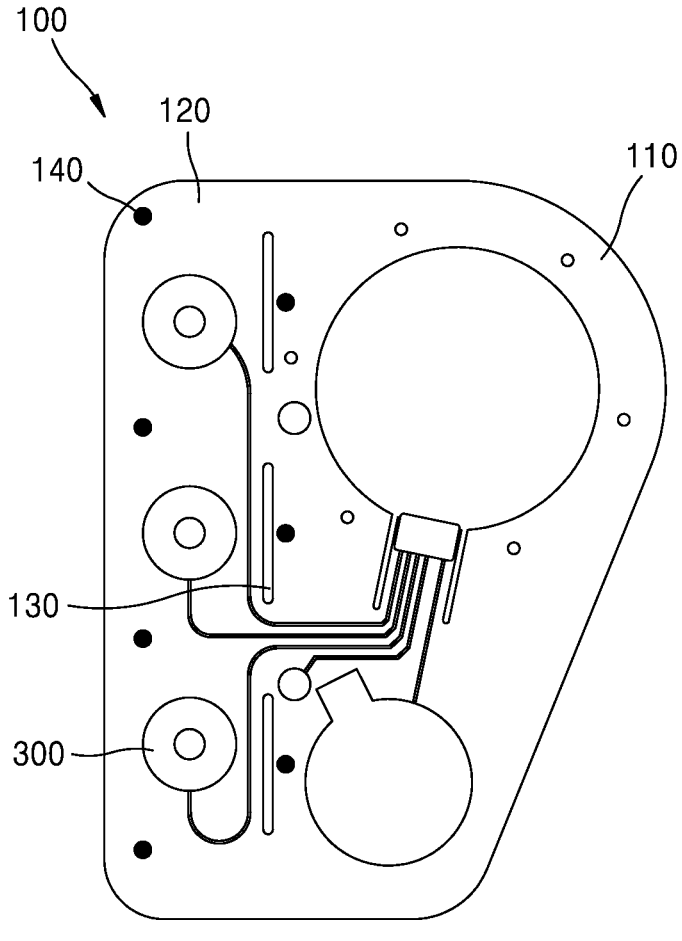
FIG. 5 is a bottom view of the skin attachment sensing electrode arranged around a sensor shown in FIG. 2.

FIG. 2 is a top-plan view of an embodiment of a bio-signal measurement patch device according to the present disclosure; FIG. 3A is a right-side view of the bio-signal measurement patch device according to an embodiment of the present disclosure; FIG. 3B is a right-side view of the bio-signal measurement patch device according to another embodiment of the present disclosure; FIG. 4 is a bottom view of a skin attachment sensing electrode 140 arranged in a first region 110 shown in FIG. 2; and FIG. 5 is a bottom view of the skin attachment sensing electrode 140 arranged around a sensor shown in FIG. 2.

As shown in the aforementioned drawings, an embodiment of the present disclosure may include a substrate 100, which includes a flexible material, and a housing 200 and one or more bio-signal measurement sensing electrodes 300 arranged on the substrate 100. In FIG. 3A, a plurality of bio-signal measurement sensing electrodes 300 are located and the present disclosure is not limited. In FIG. 3A, a bio-signal measurement sensing electrode 300 is located at a top side of the substrate 100. In other embodiments, the bio-signal measurement sensing electrode 300 may be located at the bottom side depending upon a sensing signal, as shown in FIG. 3B. The bio-signal measurement sensing electrode 300, which measures a bio-signal by sensing a voltage (e.g. ECG), may be attached to a skin (a bottom side). In a case that the bio-signal measurement sensing electrode 300 includes a module (such as an acoustic module), it may be located to the top side as shown in FIG. 3A.

The substrate 100 may include a flexible material, and may be flexibly bent according to curves of a human body and be wearable in various manners including an attached manner. The substrate 100 is a component configured to provide electricity to a sensor and receive a signal from the sensor, and in some embodiments, a circuit may be formed on the substrate 100. In some embodiments, the substrate 100 may include a flexible printed circuit board (FPCB), which includes a flexible material. Additionally or alternatively, the substrate 100 may include a multi-substrate, and may be formed in a type in which a common printed circuit board (PCB) is combined onto the FPCB. Here, it is preferable that the PCB is bendable and includes a narrow portion. The FPCB may include a film-type material or a water-resistant fabric material.

In various embodiments of the present disclosure, the substrate 100 may be divided into a first region 110 and a second region 120. The housing 200 may be arranged in the first region 110, and the bio-signal measurement sensing electrode 300 may be arranged in the second region 120. That is, the substrate 100 may be divided such that the housing 200 is arranged on one side and the bio-signal measurement sensing electrode 300 is arranged on another side. The bio-signal measurement sensing electrode 300 may be disposed on a surface in contact with a skin of a patient. As shown in FIGS. 3A and 3B, the bio-signal measurement sensing electrode 300 may be disposed on the front or rear surface of the substrate 100.

A housing arrangement hole 111 may be formed in the first region 110 in a penetrating manner for arrangement of the housing 200. The housing arrangement hole 111 may include a portion to allow electricity to be supplied to parts installed in the housing 200 that require electricity from the human body. In addition, the housing arrangement hole 111 may correspond to a form of the entire portion of the housing 200 or a portion thereof.

In some embodiments, a housing fixing hole 112 (shown in FIG. 4) may be formed in a penetrating manner and a plurality of housing fixing hole 112 is arranged to surround the housing arrangement hole 111. The housing 200 and the substrate 100 may be combined together by making a fixing structure using the housing fixing hole 112 or inserting protrusions formed in the housing 200 into the housing fixing hole 112.

In some embodiments, a separator 113 shown in FIG. 4 may be formed on a side of the housing arrangement hole 111. The separator 113 is shown in FIG. 4, and may be formed at a portion in which the housing 200 and other electric components are electrically connected. In some embodiments, the separator 113 is formed in the form of a rectangular hole on the substrate 100, and a portion of the rectangular hole may be formed to penetrate the housing arrangement hole 111. Therefore, even when deformation occurs to or in the substrate 100, an external force causing the deformation may not be delivered into the housing 200 due to the separator 113 and thus, endurability may be improved.

The bio-signal measurement sensing electrode 300 may be arranged in the second region 120. An area of the substrate 100 excluding the second area 120 may be the first area 110. The bio-signal measurement sensing electrode 300 will be described later.

In some embodiments, at a portion from which the substrate 100 is divided into the first region 110 and the second region 120, a slit 130 may be formed to make the division. As depicted in FIGS. 2, 3A and 3B, one or more slits 130 may be formed along a boundary between the first region 110 and the second region 120. That is, the substrate 100 may be divided in a vertical direction (i.e., perpendicular to the substrate 100) into the first region 110 and the second region 120, and the slit 130 may also be formed in the vertical direction. In some embodiments, one or more slits are formed in the substrate 100 to penetrate the substrate 100 and divide the first region 110 and the second region 120. A plurality of slits 130 may be serially formed as depicted in FIG. 2, and accordingly, a bridge 131 connecting the first region 110 and the second region 120 may be formed between the plurality of slits 130. Although the slit 130 is shown in single direction for convenience, the plurality of slits 130 may be embodied in various angles in other embodiments.

According to embodiments of the present disclosure, the first region 110 of the substrate 100, in which the housing 200 is arranged, may be lower than a center of the substrate, and the second region 120 in which the sensor is arranged may be arranged higher than the center of the substrate. For instance, the first region 110 of the substrate 100 may be located downward relative to the slits 130 and the second region 120 may be located upward relative to the slits 130 upon attachment of the bio-signal measurement patch device to a user, i.e., when a user wears the bio-signal measurement patch device. The housing 200 is formed of a material having a high rigidity to protect internal components, and accordingly, a weight of a body of the housing 200 and weights of the internal components are summed up to form a portion having a weight greater than those of other portions. Accordingly, when the first region 110 and the second region 120 are arranged in a horizontal direction (e.g., side by side), due to a weight of the housing 200, the first region 110 may be torn off from the skin and then, the second region 120 may be consecutively torn off from the skin. Likewise, when the first region 110 is in a lower portion and the second region 120 is in an upper portion, the first region 110 may also be torn off from the skin. And, the second region 120 may be consecutively torn off from the skin. On other way, the second region 120 may also be torn off from the skin. And, the first region 110 may be consecutively torn off from the skin. Accordingly, the first region 110 and the second region 120 may be respectively arranged in the lower portion and the upper portion to prevent separation of the second region 120 from the skin due to the weight of the housing 200. Here, the lower portion may be arranged in a leg direction and the upper portion may be arranged in a head direction.

In various embodiments, the present disclosure may include an alarm unit in the housing 200 or on the substrate 100. The alarm unit may be controlled to generate visual or audio alarms through a lamp or a speaker when a magnitude or frequency of a respiration signal or an electrocardiogram signal decreases.

In various embodiments, the skin attachment sensing electrode 140 may be arranged on the substrate 100. The skin attachment sensing electrode 140 may be configured to detect a potential difference with a reference electrode 210 to be described above, and may be configured to determine a normal attachment state and an attachment quality of the bio-signal measurement patch of the present disclosure by using a difference between a capacitance in a state of contacting the human body or a capacitance in a state of not contacting or not correctly contacting the human body.

The skin attachment sensing electrode 140 is shown in FIGS. 4 and 5. As shown in FIG. 3A, the skin attachment sensing electrode 140 may be attached onto a surface of the substrate 100, that is, a surface contacting the human body. In other embodiments, as shown in FIG. 3B, the skin attachment sensing electrode 140 may be attached to the rear surface of the substrate 100, which is a surface in contact with the human body.

Referring to the description, in some embodiments, the skin attachment sensing electrode 140 may be arranged in the first region 110, as shown in FIG. 4. However, in this case, the skin attachment sensing electrode 140 may be arranged near the slit 130. That is, a distance between the skin attachment sensing electrode 140 and the slit 130 may be less than a distance between the skin attachment sensing electrode 140 and a center of the housing 200. This arrangement of the skin attachment sensing electrode 140 near the second region 120 facilitates that the second region can be accurately attached to the skin. Furthermore, accuracy of measurement of a potential difference may improve by securing a distance between the reference electrode 210 and the skin attachment sensing electrode 140, considering that the reference electrode 210 is in the housing 200.

In another embodiment, a plurality of skin attachment sensing electrodes 140 may be arranged at a portion surrounding a plurality of bio-signal measurement sensing electrodes 300, as shown in FIG. 5. In addition, when the plurality of bio-signal measurement sensing electrodes 300 are arranged, the plurality of skin attachment sensing electrodes 140 may be alternately arranged with respect to the plurality of bio-signal measurement sensing electrodes 300. Furthermore, a position of one or more of the plurality of skin attachment sensing electrodes 140, which is determined as not being attached to the skin, may be transmitted to a monitoring device through a communicator. By doing so, a portion warping or an unattached portion may be detected.

As shown in FIG. 4, the battery 150 may be mounted on the substrate 100 and protected by the housing 200, or may be mounted in the housing 200. FIG. 4 illustrates that the battery 150 is mounted on the substrate 100.

As shown in FIG. 4, the housing 200 may be arranged in a housing arrangement hole 111 in the first region 110 of the substrate 100. The housing 200 may include a communicator (not shown) configured to collecting information measured from the battery 150 and the sensor and transmitting the information to the monitoring device. The communicator may include an ID for Bluetooth connection. The bio-signal measurement patch device may further include an alarm unit and a controller configured to control the aforementioned components.

In various embodiments, the housing 200 may be formed of a plastic jet and has a certain thickness, as the battery 150 and the like are arranged in the housing 200. Accordingly, the housing 200 protrudes more than other portions of the substrate 100, as depicted in FIGS. 3A and 3B. Thus, it is structured to be more easily attached to a human body when pushed toward the human body. Accordingly, when a respiration sensor configured to detect sound is mounted, the respiration sensor may be mounted in the housing 200.

In addition, as depicted in FIG. 3A, the reference electrode 210 may be mounted in the housing 200. Together with the skin attachment sensing electrode 140 described above, the reference electrode 210 is configured to measure an attachment quality of the bio-signal patch device according to the present disclosure. The reference electrode 210 may be attached onto the front surface of the substrate 100, i.e., the surface contacting the human body, as depicted in FIG. 3A.

In some embodiments, the bio-signal measurement sensing electrode 300 may measure bio-signals, and may include, e.g., a respiratory sensor, an electrocardiogram sensor, a snore sensor, a tossing-and-turning sensor, and an electromyogram (EMG) sensor. As shown in FIG. 3A, the bio-signal measurement sensing electrode 300 may be implemented with three electrodes, but it is not limited thereto and may be implemented with two or more electrodes. The bio-signal measurement sensing electrode 300 may add a sensor (e.g. accelerometer) or a module (e.g. acoustic, photoplethysmography).

In some embodiments, the respiratory sensor is a sensor configured to sense a potential difference according to contraction and expansion of a heart using an electrocardiogram (ECG) electrode. The respiratory sensor may detect a heart frequency, arrhythmia, and the like using the potential different sensed.

The respiratory sensor configured to sense sounds especially needs to be attached to the human body. Therefore, the respiratory sensor may be mounted in the housing 200, which is more easily attached to the human body than the substrate 100 when being pushed. The respiratory sensor, which is configured to sense a capacitor, is a sensor configured to measure changes in a capacitance according to contraction and expansion of a volume of a thoracic cage during respiration. The changes in the capacitance may also be measured by the skin attachment sensing electrode 140. A respiration rate per hour may be calculated using a change cycle of the capacitance.

In some embodiments, a snore sensor, which is a type of acoustic sensor, is a sensor configured to recognize a snoring sound and an apnea state. Additionally or alternatively, a tossing-and-turning sensor, which is a type of an acceleration sensor or a gyro sensor, may measure a degree of tossing-and-turning according to a degree of posture change by sensing posture changes of the user. An electromyogram sensor, which is configured to measure a potential difference between EMG electrodes, like an ECG electrode, may sense an electric signal used for muscle movements. Additionally, the bio-signal measurement sensing electrode 300 may further include a temperature sensor and an impedance sensor.

Referring back to FIGS. 4 and 5, the battery 150, the skin attachment sensing electrode 140, and the bio-signal measurement sensing electrode 300 are electrically connected to the components in the housing 200 through wires 310 on the substrate 100, and may be especially connected through a connector 320. The connector 320 may be mounted near the separator 113 of the aforementioned substrate 100 and protected from an external force, and it is preferable that the separator 113 is formed at each of two sides of the connector 320.

In various embodiments, an attachment patch 400, as depicted in FIGS. 3A and 3B, may be attached to a rear surface of the substrate 100. The attachment patch 400 may include a patch, a surface of which is coated with an adhesive, or may include an adhesive film. As shown in FIG. 3A, the attachment patch 400 is formed in a size greater than a size of the substrate 100, such that the attachment patch 400 may protect the substrate 100 and an edge portion of the attachment patch 400 may be attached to the human body. Therefore, the attachment patch 400 may be formed such that a rear surface thereof is non-attachable and a front surface 400 thereof may be attached. A sheet of release paper may be attached to the front surface of the attachment patch 400, and the release paper may be removed right before use. As shown in FIG. 3B, the adhesive patch 400 may be formed as much as a partial area of the substrate 100 and may be modified in various ways without being limited thereto.

Hereinafter, a method of using the bio-signal measurement patch device according to an embodiment of the disclosure will be described. A method of using the bio-signal measurement patch device relates to a method of using the bio-signal measurement patch device described above, and same names and reference numerals may be understood as having same meanings. However, it is not deemed that only implementation including all components of the bio-signal measurement patch device is within the scope of the disclosure, and implementation only including some of the components may be within the scope of the disclosure.

Figure 6:
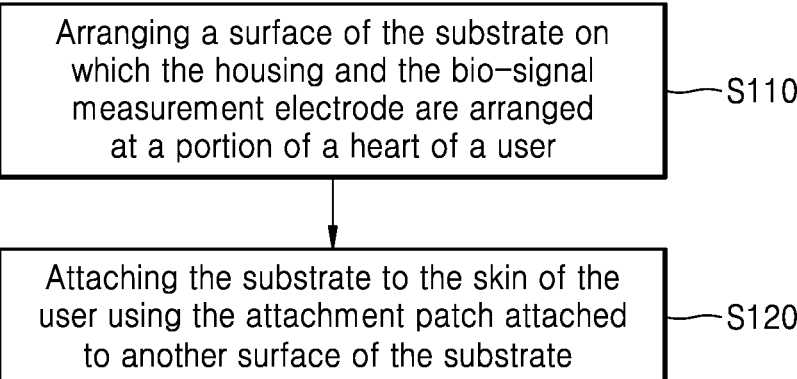
FIG. 6 is a flowchart illustrating a method of using the bio-signal measurement patch device, according to embodiments.

FIG. 6 is a flowchart illustrating a method of using the bio-signal measurement patch device, according to embodiments.

In various embodiments, the method of using the bio-signal measurement patch device may include: a substrate arrangement operation of arranging a surface of the substrate 100, on which the housing 200 and the bio-signal measurement sensing electrode 300 are arranged at a portion of a heart of the user (S110), and an attachment operation of attaching the substrate 100 to the skin of the user using the attachment patch 400 attached to another surface of the substrate 100 (S120). Here, the portion of the heart does not indicate an accurate position of the heart and rather indicates the entire thorax near the heart. Here, one surface of the substrate may be a surface on which the bio-signal measurement sensing electrode 300 is disposed.

Figure 7:
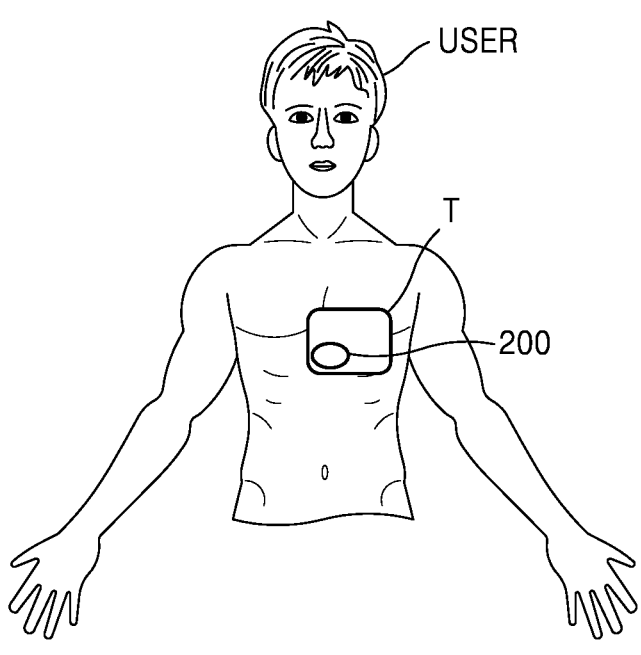
FIG. 7 is an example drawing of a bio-signal measurement patch device attached to a user's skin according to embodiments.

FIG. 7 is an example drawing of a bio-signal measurement patch device attached to a user's body according to embodiments.

In the arranging of the substrate 100, the substrate 100 may be arranged such that the first region 110 of the substrate 100 is at a position lower than a position of the second region 120. The bio-signal measurement patch device T may be attached near the user's heart in a direction in which the housing 200 is located lower than other parts of the substrate 100. This is to prevent the second region 120 of the substrate 100 from being separated off of the skin by the weight of the housing 200, because the housing 200 is a relatively heavy component on the substrate 100.

Specific technical descriptions in the embodiments are only examples and are not to limit the technical range of the embodiments. For brevity and clarity of description of the disclosure, descriptions regarding existing art and components may be omitted. In addition, connection between lines between the components in the drawing or connection members are examples of functional connection and/or physical or circuitry connections, and in actual devices, may be substituted or expressed as various additional connections, e.g., functional connection, physical connection, or circuitry connection. Furthermore, unless a component is specifically mentioned such as "essential," "importantly", the component may not be a necessary component for application of the disclosure.

Unless specifically defined, a designator such as "the" or similar thereto used in the description and the claims may encompass a singular form and a plural form. In addition, when a range is written in an embodiment, the embodiment includes a disclosure in which an individual value within the range (unless otherwise written), this corresponds to writing individual values within the range in the detailed description. Furthermore, when there are no clear descriptions or opposite descriptions of operations included in a method according to embodiments, the operations may be performed in an appropriate order. The embodiments are not limited to the order of descriptions of the operations. Use of all examples or example terms (e.g., and the like) in the embodiments are merely to describe the embodiments in detail, and unless the embodiments are limited by the claims, the range of embodiments are not limited by the examples or example terms. In addition, it is obvious to those skilled in the art that various correction, combination, and modification may be established according to design conditions and factors within the following claims and a category of equivalents thereof.

According to the method of the disclosure, various effects including the following may be expected. However, the disclosure is not necessarily established only when all of the following effects are obtained.

A bio-signal measurement patch device according to an embodiment, in which a substrate may be deformed to correspond to curves and motions of human body skin by forming slits between a housing and a bio-signal sensing sensor, may maintain attachment thereof by attaching, to the skin, sensors configured to measure bio-signals.

In addition, according to the disclosure, it is possible to promptly response to separation of the patch from the skin by accurately detecting by the skin attachment sensing electrode whether the sensors are closely attached to the skin.

Furthermore, according to the disclosure, as respiration, snoring, tossing-and-turning may be sensed, and an alarm is issued when the respiratory signal or the electrocardiogram signal decreases, therefore, it is possible to easily perform monitoring and rapidly cope with emergencies.

In addition, according to the disclosure, the first region of the substrate in which the housing is arranged in the lower portion, and the second region in which the sensor is arranged is arranged in the upper portion, and therefore, it is possible to prevent separation of the second region from the skin due to the weight of the housing.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A bio-signal measurement patch device comprising:
    a substrate including a flexible material, the substrate having a first region and a second region;
    a housing disposed on the first region of the substrate, and including a communicator;
    one or more bio-signal measurement sensing electrodes disposed on the second region of the substrate;
    one or more slits defined in the substrate and penetrating the substrate, the one or more slits dividing the substrate into the first region and the second region;
    a reference electrode disposed on the substrate or on the housing;
    a skin attachment sensing electrode disposed on the substrate and configured to measure an attachment quality of the one or more bio-signal measurement sensing electrodes according to changes in a capacitance of the skin attachment sensing electrode and the reference electrode;

a housing arrangement hole defined in the first region and penetrating the substrate, the housing arrangement hole having a shape corresponding to at least a portion of the housing and configured to accommodate the housing inserted therein;

at least one separator defined in the first region of the substrate directly adjacent to the housing arrangement hole, and penetrating the substrate; and a battery disposed on the substrate, wherein at least a portion of the at least one separator communicates with the housing arrangement hole, wherein the at least one separator is configured to prevent an external force applied to the substrate from being delivered to the housing, thereby preventing deformation of the housing, wherein the at least one separator includes two separators parallel to each other, wherein the reference electrode is disposed on the housing, wherein the one or more bio-signal measurement sensing electrodes, the skin attachment sensing electrode, and the battery are electrically connected to the reference electrode disposed on the housing via wires and a connector, wherein the connector is disposed adjacent to the housing arrangement hole, wherein each of the two separators is defined at a respective side of the connector, and wherein the communicator is configured to transmit, to a monitoring device via wireless connection, data indicating a position of the skin attachment sensing electrode determined to be detached from a skin based on the measured capacitance.

2. The bio-signal measurement patch device of claim 1, wherein the one or more slits further comprise a plurality of slits that are serially defined in a predetermined direction, and further comprising a bridge connecting the first region to the second region arranged between the plurality of slits.

3. The bio-signal measurement patch device of claim 1, further comprising a plurality of skin attachment sensing electrodes disposed at a position surrounding the one or more bio-signal measurement sensing electrodes.

4. The bio-signal measurement patch device of claim 3, wherein the one or more bio-signal measurement sensing electrodes further comprise a plurality of bio-signal measurement sensing electrodes, and the plurality of skin attachment sensing electrodes are alternately disposed between the plurality of bio-signal measurement sensing electrodes.

5. The bio-signal measurement patch device of claim 1, wherein the reference electrode is disposed on the first region or the housing, and the skin attachment sensing electrode is disposed on the second region.

6. The bio-signal measurement patch device of claim 1, wherein the skin attachment sensing electrode is additionally disposed on the first region, and a distance between the skin attachment sensing electrode disposed on the first region and the one or more slits is less than a distance between the skin attachment sensing electrode and a center of the housing.

7. The bio-signal measurement patch device of claim 1, wherein the one or more bio-signal measurement sensing electrodes comprise a respiratory sensor, an electrocardiogram sensor, a snore sensor, a tossing-and-turning sensor, an electromyogram sensor, a temperature sensor, and an impedance sensor, or a combination thereof.

8. The bio-signal measurement patch device of claim 1, wherein, when the bio-signal measurement patch device is attached to the skin of a user, the first region is positioned in a lower region of the substrate, and the second region is positioned in an upper region of the substrate.

9. The bio-signal measurement patch device of claim 1, further comprising:

a plurality of housing fixing holes defined in the substrate, surrounding the housing arrangement hole, and penetrating the substrate, wherein the housing includes a plurality of protrusions configured to be inserted into the plurality of housing fixing holes, and wherein engagement between the plurality of protrusions and the plurality of housing fixing holes secures the housing within the housing arrangement hole.

10. The bio-signal measurement patch device of claim 1, wherein the at least one separator has an elongated shape.

11. The bio-signal measurement patch device of claim 1, wherein the at least one separator has a rectangular shape.

12. The bio-signal measurement patch device of claim 1, wherein the at least one separator extends outward from a center of the housing arrangement hole.

13. The bio-signal measurement patch device of claim 1, wherein the communicator uses a short-range wireless connection.

* * * * *